(12) United States Patent
Floor (10) Patent No.: US 11,442,005 B2
(45) Date of Patent: Sep. 13, 2022

(54) GAS ANALYSER SYSTEM

(71) Applicant: FLO2R ApS, Hadsund (DK)

(72) Inventor: Karsten Brink Floor, Hadsund (DK)

(73) Assignee: FLO2R APS, Hadsund (DK)

( * ) Notice: Subject to any disclaimer, the term of this patent is extended or adjusted under 35 U.S.C. 154(b) by 41 days.

(21) Appl. No.: 17/074,051

(22) Filed: Oct. 19, 2020

(65) Prior Publication Data

US 2021/0033524 A1 Feb. 4, 2021

Related U.S. Application Data

(63) Continuation of application No. PCT/EP2018/060195, filed on Apr. 20, 2018.

(51) Int. Cl.
  *B01D 46/71* (2022.01)
  *G01N 21/31* (2006.01)
  (Continued)

(52) U.S. Cl.
  CPC .............. *G01N 21/31* (2013.01); *B01D 46/71* (2022.01); *G01K 13/00* (2013.01); *G01L 13/00* (2013.01);
  (Continued)

(58) Field of Classification Search
  CPC ...... G01N 21/31; G01N 1/44; G01N 33/0006; G01N 2201/06113; G01N 2021/151;
  (Continued)

(56) References Cited

U.S. PATENT DOCUMENTS 3,787,122 A * 1/1974 Lepper, Jr. ............. G01N 21/53
  356/439
4,113,386 A * 9/1978 Lepper, Jr. ............. G01N 21/53
  356/442
(Continued)

FOREIGN PATENT DOCUMENTS

CN          2 692 660 Y      4/2005
CN        101 620 181 A      1/2010
(Continued)

OTHER PUBLICATIONS

International Search Report and Written Opinion regarding PCT/EP2018/060195 dated Jan. 30, 2019, 21 pages.
(Continued)

*Primary Examiner* — David J Bolduc
(74) *Attorney, Agent, or Firm* — Crowell & Moring LLP (57) ABSTRACT

An extractive gas analyser system includes a supply channel, a measuring channel connected thereto between first and second ends, an analysing unit comprising an optical arrangement for analysing gaseous material in the measuring channel, which optical arrangement comprises first and second optical units arranged respectively at first and second ends of the measuring channel, a barrier arrangement near each end of the measuring channel and comprising a barrier gas inlet and outlet arranged in opposing manner across said measuring channel, each in connection with a gas source and provided with a nozzle opening directed toward the opposing outlet, said barrier arrangement arranged to provide pressurized gas creating a barrier gas curtain between the barrier gas inlet and outlet to force least a part of the gaseous material from the supply channel into the measuring channel and out through the outlet and thereby separate the gaseous material from said optical units.

20 Claims, 4 Drawing Sheets

(51) Int. Cl.
*G01K 13/00* (2021.01)
*G01L 13/00* (2006.01)
*G01N 1/44* (2006.01)
*G01N 33/00* (2006.01)
*G05D 16/20* (2006.01)

(52) U.S. Cl.
CPC .......... *G01N 1/44* (2013.01); *G01N 33/0006* (2013.01); *B01D 2279/00* (2013.01); *G01N 2201/06113* (2013.01); *G05D 16/2066* (2013.01)

(58) Field of Classification Search
CPC .. G01N 21/05; G01N 21/3504; G01N 21/031; B01D 46/71; B01D 2279/00; G01K 13/00; G01L 13/00; G05D 16/2066
See application file for complete search history.

(56) References Cited

U.S. PATENT DOCUMENTS

| | | | | |
|---|---|---|---|---|
| 5,135,304 | A * | 8/1992 | Miles | G01N 21/15 |
| | | | | 250/576 |
| 5,245,405 | A * | 9/1993 | Mitchell | G01N 21/15 |
| | | | | 356/245 |
| 5,374,992 | A * | 12/1994 | Pye | G01N 21/534 |
| | | | | 356/439 |
| 5,452,084 | A * | 9/1995 | Mitchell | G01N 21/65 |
| | | | | 250/282 |
| 5,701,012 | A * | 12/1997 | Ho | G01N 21/64 |
| | | | | 250/461.2 |
| 5,929,981 | A * | 7/1999 | Keilbach | G01N 21/15 |
| | | | | 356/73 |
| 7,377,185 | B2 * | 5/2008 | Kawanishi | G01F 7/00 |
| | | | | 123/406.12 |
| 7,647,844 | B2 * | 1/2010 | Kawanishi | G01F 5/00 |
| | | | | 73/202.5 |
| 8,358,411 | B2 * | 1/2013 | Babico | G01N 21/49 |
| | | | | 356/336 |
| 8,570,520 | B2 * | 10/2013 | Fleischer | G01N 21/3504 |
| | | | | 356/437 |
| 9,116,047 | B2 * | 8/2015 | Koulikov | G01J 3/45 |
| 9,678,003 | B2 * | 6/2017 | Koulikov | G01N 21/59 |
| 9,719,910 | B2 * | 8/2017 | Irie | G01N 15/1459 |
| 2003/0071218 | A1 * | 4/2003 | Nakamura | G01N 21/3504 |
| | | | | 250/343 |
| 2007/0180893 | A1 * | 8/2007 | Floor | G01N 1/2205 |
| | | | | 73/28.01 |
| 2010/0165341 | A1 * | 7/2010 | Babico | G01N 15/1459 |
| | | | | 356/336 |
| 2013/0161544 | A1 * | 6/2013 | Ohnishi | G01N 21/3504 |
| | | | | 250/564 |
| 2013/0248693 | A1 * | 9/2013 | Buchanan, III | G01N 15/0211 |
| | | | | 250/222.2 |
| 2014/0223999 | A1 * | 8/2014 | Graehlert | G01N 15/0826 |
| | | | | 73/38 |
| 2014/0340681 | A1 * | 11/2014 | Murakami | G01N 21/51 |
| | | | | 250/435 |
| 2015/0346074 | A1 * | 12/2015 | Irie | G01N 15/1404 |
| | | | | 356/338 |
| 2017/0284923 | A1 * | 10/2017 | Irie | G01N 15/1404 |
| 2019/0321534 | A1 * | 10/2019 | Von Blumenthal | A61B 5/14557 |
| 2020/0264094 | A1 * | 8/2020 | Floor | G01N 21/8507 |

FOREIGN PATENT DOCUMENTS

| | | | | |
|---|---|---|---|---|
| CN | 201 795 990 | U | 4/2011 | |
| EP | 2 803 976 | A1 | 11/2014 | |
| EP | 2803976 | A1 * | 11/2014 | .......... G01N 21/031 |
| JP | H11 295213 | A | 10/1999 | |
| KR | 2009 0034485 | A | 4/2009 | |
| WO | WO2011/143304 | A2 | 11/2011 | |
| WO | WO-2011143304 | A2 * | 11/2011 | ............ G01N 15/06 |

OTHER PUBLICATIONS

International Preliminary Report on Patentability regarding PCT/EP2018/060195 dated Jul. 3, 2020, 71 pages.

\* cited by examiner

GAS ANALYSER SYSTEM

CROSS-REFERENCE TO RELATED APPLICATIONS

This application claims priority as a Continuation of PCT/EP2018/060195, filed Apr. 20, 2018, which is incorporated by reference herein in its entirety.

TECHNICAL FIELD

The invention relates to a system for analysis of a gas, such as a flue gas and to a method of analysis of a gas using a gas analyser.

BACKGROUND

Gas analyser systems are known to be used for real-time analysis of exhaust gasses and flue gasses from furnaces, engines, boilers etc. The analysis provides for increased insight in the combustion process and allows for efficient adjustment and control of the process. A gas analyser using an optical analysing unit for quantitative gas analysis is capable of providing concentration data for different species contained in the flue gas. A light source, such as a laser, directs electromagnetic beam through a gaseous sample and towards a receiver at which the beam is collected. Based on the received beam an absorption spectrum can be calculated, showing selective light absorption by the species present. The information contained in the measured spectrum can, among other things, yield quite accurate information about the concentration of species, such as molecules, present. At selected wavelengths, known to be associated with species in question, a measure of the light intensity and the travelled distance of the light signal can be utilized to provide concentration information about the specie. It's a continuous desire within the technical field to improve and optimise gas analyser for these types of measurements, with the aim of improving aspects such as accuracy, time and cost associated with these measurements.

Generally, there exist two different types of gas analysers for flue gas characterisation, an in situ analyser and an extractive analyser. The in situ analyser measures the gas material in its gaseous environment, typically in a chimney. In situ analysers can measure cross-duct, that is having the light beam transmitting across the chimney, or by using a probe having an elongated housing extending a distance into the chimney and comprising optical components at each end of the housing. Benefits of using an in situ analyser includes measuring under actual process conditions, limiting possible negative influences of analyser-setup on the gas material to be measured. Typically an in situ gas analyser also comprises a simplistic design and is thereby cost efficient. On the other hand, in situ analysers and their optical components are usually difficult to maintain, experience constrains in relation to the number of species that can be measured simultaneously and furthermore can be difficult to calibrate.

An extractive gas analyser, extracts gas material from the gaseous environment such as within a chimney, and typically directs the gas material through a filter and to a measuring chamber outside the chimney, where the gas is analysed. As the gas analyser is positioned outside the chimney it is usually highly accessible readily operable. Advantageously optical arrangements of extractive systems are also easy to align and calibrate. On the other hand extractive systems are usually quite complex as it is desirable to be able to maintain the gaseous material in a condition similar to the condition of the material at the point of extraction. Furthermore the transport of the sample to the measuring chamber results in longer response-times of the system.

For optical measurements of a gaseous material which may contain a high level of dust and corrosive species, it has been shown to be inefficient and difficult to measure gas samples from a gaseous environment of high dust content, as only a small fraction of the light beam reaches the receiver. Furthermore, in such gaseous environments of high dust content and especially in hazardous and possibly chemically aggressive gaseous environments, it is necessary to protect the optical components, for example by providing purge gas on optical windows. In JP patent document no. 3186602 an extractive gas analyser is shown, which utilized purge air introduced in front of the optical components. Such purge air setups which introduce a second gaseous material in the measuring chamber, are generally disadvantageous due to difficulties in controlling the consistency and efficiency of the purging process but also in controlling the degree of influence such purge gas has on the gas volume to be measured, which in turn affects the accuracy of the optical measurement.

One of the objects of the present invention is to provide an extractive gas analyser system which is efficient in significantly reducing the risk of contamination of components of the gas analyser system, especially the optical parts of the system, and simultaneously providing a gas analyser allowing for optical measurements of high accuracy. A further object of the invention is to provide a stable and simplified gas analyser system, which is easy to control and operate. Providing a gas analyser system which can analyse gaseous material extracted from environment of high dust content is also an object of the invention. Another object of the invention is to provide an extractive gas analyser system providing fast analysis of gaseous material with low response-time.

BRIEF DESCRIPTION OF THE INVENTION

The first aspect of the invention relates to a gas analyser system for extractive measurement of a gaseous material, wherein the gas analyser system comprises a supply channel having an inlet supply opening at a first end and one or more outlet supply opening(s) at a second end of the channel, and a measuring channel connected to said supply channel between said first and second end, an analysing unit, comprising an optical arrangement for analysing said gaseous material contained in said measuring channel, wherein the optical arrangement comprises a first optical unit arranged at a first end of the measuring channel and a second optical unit arranged at a second end of said measuring channel, a barrier arrangement arranged near each end of the measuring channel comprising a barrier gas inlet and a barrier gas outlet arranged in opposing manner across said measuring channel, each barrier gas inlet is in connection with an gas source, such as an air source, and provided with a nozzle having a nozzle opening being directed towards said opposing barrier gas outlet having a barrier gas outlet opening, said barrier arrangement is arranged to provide pressurized gas creating a barrier gas curtain between said barrier gas inlet and said barrier gas outlet so as to force least a part of said gaseous material from said supply channel into said measuring channel and out through said barrier gas outlet and so as to separate the gaseous material from said optical units.

Advantageously, the gas analyser system according to the present invention comprising an air curtain provides a combination of several benefits. The barrier gas curtain of pressurized gas not only efficiently provides a separation between the gaseous material to be analysed and optical units, but furthermore simultaneously ensures that the measuring channel is continuously supplied and filled by the gaseous material. When pressurized gas is discharged e.g. when the barrier gas enters the measuring channel, this movement creates an area of low pressure at the expanding side of the nozzle which pulls gas molecules into the flow from the supply channel via the measuring channel. The gaseous material is preferably eventually entrained by the barrier gas curtain and discharged with the barrier gas curtain through the barrier gas outlet. Advantageously, the gas analyser is provided with an opposing barrier gas outlet for avoiding any mixing of the barrier gas with the gaseous material further into the measuring channel toward the connection between the supply channel and the measuring channel.

The difference in pressure (dP_mc) created gas along the measuring channel is preferably continuously maintained in order to as to provide a continuous flow of gas material which advantageously provides a gas analyser which allows for low response-times. Changes in the content of the gaseous environment, from which environment the gas material is extracted are therefore quickly analysed. Advantageously, the pressure difference (dP_mc) created in the measuring channel furthermore eliminates the risk of undesirable and uncontrolled flow of barrier gas into the measuring channel towards the supply channel, which can reduce the accuracy of the measurements. The present gas analyser system provides a barrier gas arrangement which advantageously prevents potential contamination of optical parts and furthermore prevents dilution of gaseous material in the measuring channel, due to the large control of gas flows through the system.

As the barrier gas curtain can isolate the optical units, the durability of optical components is improved, making the gas analyser more stable, easy to maintain which has a major effect on not only the cost of the system but also on the accuracy of the analyser measurements.

The provided difference in pressure along the measuring channel further allows for the gaseous material to be evenly distributed along the longitudinal extend of the measuring channel, meaning that the optical arrangement measures on a homogenous volume of gaseous material which is highly beneficial for the resulting accuracy of the gas analysis. For the gas analysis the travelled distance of the electromagnetic light through the gaseous material is needed as well as the light intensity of selected wavelength(s) after interacting with the gaseous material. If the gaseous material is unevenly distributed, the travelled distance of the electromagnetic light may not be the actual distance the electromagnetic light has travelled through the gaseous material, increasing the uncertainties on the results of the analysis.

Introducing a second gaseous material in the measuring channel may introduce a larger uncertainty in the measurement of light intensity and also in the measurements of the travelled distance. Additionally or alternatively, the actual distance along which the electromagnetic light has interacted with the gaseous material can vary with changes in the volume of isolation gas between the optical units and the gaseous material. Advantageously by the present invention, the thickness of the barrier gas curtain can be precisely controlled and therefore the thickness of the barrier gas curtain is well defined, which in turn increases the accuracy of the analysis results. Furthermore, by the present setup the barrier gas thickness (T_bg) may advantageously be independent of changes in flow rate through the supply channel, meaning that any change in pressure difference (dP_s) in the supply channel has no effect on the accuracy of the actual measured distance for the gas analysis.

As the barrier gas curtain is relatively thin the barrier gas air consumption is also low compared to systems using flushing air providing gas isolation zone or a gas curtain. Furthermore the curtain thickness only takes up a small percentage of the total distance travelled by the electromagnetic radiation in the measuring channel, thereby having a smaller effect on the uncertainties that may be associated with the measurement.

In one or more embodiments, the gaseous material may be exhaust gas, tail gas or flue gas. The gaseous material may contain gaseous acids, which can be damaging to the gas analyser system components, e.g. condensed acid on may be corrosive. The gaseous material may contain particulates such as carbon monoxide (CO), nitrogen oxides (NOx), and gaseous sulfur oxides such as sulfur dioxide (SO2) and sulfur trioxide (SO3). E.g. a combination of the gaseous SO3 with H2O vapor can lead to forming sulfuric acid (H2SO4) which is corrosive, additionally or alternatively, nitric acid may also be formed. In one or more embodiments the acid-resistant steel is used for the inner surfaces of the channels in the gas analyser system. Advantageously the barrier gas curtain prevents contact between the gaseous material and the optical units.

In one or more embodiments, said measuring channel may be in connection to said supply channel so as to provide a four-channel intersection, e.g. the longitudinal axis of the measuring channel may preferably be arranged perpendicular to the longitudinal axis of the supply channel, at a point between the first and second end of the supply channel. This allows for a simplified setup in which the measuring channel can be arranged symmetrically about the longitudinal axis of the supply channel, ensuring equal physical conditions in the measuring channel on each side of the supply channel. The first end of the supply channel preferably is in fluid connection with the gaseous environment. The second end of the supply channel may be in fluid connection with an outlet for discharging said gaseous material.

In one or more embodiments, the pressure difference (dP_mc) is constantly provided such that the area of lowest pressure is near the barrier gas curtain, in order to avoid barrier gas entering the measuring channel toward the intersection.

In one or more embodiments, the gas analyser comprises a pressure system configured to provide a pressure difference (dP_1) between the first end of the supply channel and the second end of the supply channel, such as to provide a flow of gaseous material from said first end to said second end, wherein the first end of the supply channel is in connection with said gaseous environment. Preferably, the pressure difference (dP_mc) is constantly provided such that the low pressure area is near the second end of the supply channel.

In one or more embodiments the gas analyser system may further comprise a pressure system, wherein the pressure system is arranged to provide a pressure difference (dP_s), defined as the difference between a first pressure (P1) near said first end of the supply channel and a second pressure (P2) near the second end of the supply channel, wherein the first pressure (P1) is larger than the second pressure (P2).

The pressure difference (dP_s=P1−P2) so as to enabling a flow of gaseous material form a gaseous environment through the gas analyser system, such as into the supply channel, towards the intersection with said measuring channel, and towards the second end of the supply channel. Advantageously, this provides a fast uninterrupted supply of new gaseous material. The applied pressure difference is advantageous for the gas analyser system as the flow of gaseous material becomes continuous, uniform and directional through the supply channel. Furthermore the flow of gaseous material through the supply channel advantageously becomes independent of the pressure within the gaseous environment, which may vary with +/−100 mbar. Advantageously, as the pressure difference (dP_s) in the supply channel is controlled the barrier gas curtain thickness and function becomes independent of changes in pressure of the gaseous environment. In a preferred embodiment, the pressure difference (dP_s) is at least minus 10 mbar, such as minus 20 mbar or preferably such as at least minus 30 mbar (−30 mbar). In one or more embodiments, the pressure difference (DP_s) is between minus 5-100 mbar.

In one or more embodiments, the gas analyser system may comprise a first pressure sensor arranged near the first end of said supply channel so as to measure said first pressure (P1) and provide a data output accordingly to said pressure system.

The pressor sensor may be any type of pressor sensor suitable for the present purpose, and be arranged to detect a pressure and communicate said detected pressure to the pressure system. Advantageously, the pressure sensor for measuring the first pressure (P1) enables an easier control of the pressures within the supply channel, and provides information about the pressure condition of the gaseous environment to the pressure system and e.g. the operator of the system.

In one or more embodiments, the gas analyser system may comprise a second pressure sensor arranged near the second end of said supply channel so as to measure said second pressure (P2) and provide a data output accordingly to said pressure system.

A pressure sensor may be arranged so as to provide information on the second pressure to the pressure system and/or operator of the system, in order to accurately determine the pressure difference in the gas analyser system.

In one or more embodiments, the gas analyser system may comprise a control unit having a first pressure controller for controlling said second pressure (P2) based on said first and second data outputs, preferably so as to maintain said pressure difference (dP_s) substantially constant or within a predetermined range.

Advantageously, the pressure system enables a continuous control of the pressures of the system, enabling controlled flow of gaseous material through the system. In events of pressure drops in the gaseous environment, the pressure system is arranged to adjust the second pressure so as to maintain the desired pressure difference (dP_s) in the system and thereby the desired flow of gaseous material. In one or more embodiments, the first pressure controller is arranged to control said second pressure (P2) so that a pressure difference (dP_s) between minus 5 to minus 100 mbar.

In one or more embodiments, the supply channel may comprise one or more outlet openings, which may lead the gaseous material to one or more reservoirs, environments or measuring channels, after being connected to the measuring channel.

In one or more embodiments, the pressure system may comprise a pressure tank in connection to said outlet supply opening(s), and wherein the pressure tank is arranged to provide said second pressure (P2) to said outlet supply opening(s) by means of one or more pump(s).

The pressure within the pressure tank, i.e. the second pressure (P2) may be provided by means of any suitable pumps, such as an ejector pump or an electric diaphragm pump. The second pressure (P2) may be set to any pressure value along as the desired pressure difference (dP_s) is provided within the system. Advantageous, the centre flow of gaseous material through the supply chain may preferably be collected in said pressure tank. Where it may be stored, post-processed or directed to a second gas analyser. In one or more embodiments, the barrier gas curtain outlets may be in fluid connection with separate pressure tank, whereby the pressure at said barrier gas outlets may be controlled individually.

In one or more embodiments, the pressure tank is furthermore in connection to said barrier gas outlets and provides said second pressure (P2) to said barrier gas outlet by means of said one or more pump(s). The barrier gas outlet openings may preferably be in fluid connection with said pressure tank so with the barrier gas mixed with gaseous material due to the entrainment by the curtain is collected in the pressure tank together with the gaseous material from the supply channel. Advantageously low pressure within the pressure tank ensures a flow of the mixed gas from said measuring channel through said barrier gas outlet to said pressure tank.

This provides for a simplified setup for controlling the pressures within the system, wherein the pressure at all three outlet ports to the pressure tank are equal, e.g. at the second pressure (P2). Furthermore it allows for the gaseous material from the supply channel to be mixed with the barrier gas and thereby be diluted, which reduces the concentration of chemically hostile particulates in the gas. Thereafter the diluted gas is allowed to come into contact with even corrosion-sensitive components.

In one or more embodiments, the barrier arrangement may comprise curtain flow control means for controlling the flow rate of a barrier gas curtain, and thereby control the amount of gaseous material forced towards said barrier curtain.

The flow rate of the barrier gas curtain may preferably be controlled to continuously provide a third pressure (P3) at the barrier gas curtain which is lower than the pressure at the intersection between the measuring channel and the supply channel, so that part of said gaseous material is forced from said supply channel towards said barrier gas curtain. The flow rate of barrier gas curtain is preferably provided at a rate high enough to expand and simultaneously be collected by the barrier gas outlet, so the barrier gas curtain is not mixed into measuring channel. In one or more embodiments a change in the barrier gas curtain flow rate in turn changes the flow rate of gaseous material through the measuring channel, so that gaseous material in the measuring channel is more rapidly replaced. Advantageously, pressure controlled air curtain provides a small response-time of the gas analyser system, such as between 1-3 seconds.

In one or more embodiments, the gas analyser further comprises a flowmeter for detecting the flow rate of said barrier gas and provides an output to said curtain control means. The curtain control means equipped with a valve for controlling the flow rate through said nozzle and may be arranged to control said flow rate based on said output. Furthermore, the thickness of the barrier gas curtain may also be controlled by controlling the flowrate. This provides the advantages of being able to control and adjust the effect of the barrier gas thickness of the optical measurement as well as the amount of gaseous material forced into measuring channel from the centre-flow of gas material. In one or more embodiments, the flow rate of the barrier gas curtain may be set to 0.5-10 litres per minute, such as between 1-5 l/min. Preferably the barrier gas curtain is of a substantially uniform flow rate while measurements are undertaken on said gaseous material in the measuring channel.

In one or more embodiments, for every amount of gaseous material reaching said measuring channel, a fraction A between 0.01-0.6, such as between 0.1-0.4, preferably between 0.1-0.3 is forced sideways towards said barrier gas curtain.

In one or more embodiments, the fraction A forced towards the curtain and filling the measuring channel between the intersection and the curtain is up to 60% of the gaseous material entering the gas analyser system. Advantageously the gas analyser system of the present invention allows for precise control of the amount of gas to be distributed in said measuring channel, and how quick the measuring channel is updated with new gaseous material.

In one or more embodiments, for every amount of gaseous material reaching said measuring channel, a fraction B continuous across said measuring channel to said pressure tank, wherein the fraction B is between 0.40-0.99, such as between 0.6-0.9, preferably between 0.7-0.9.

In one or more embodiments the fraction B may be at least 40%, such as at least 50%, such as at least 60% of the gaseous material entering the gas analyser system. Advantageously, the amount of gas continuing to flow in the supply channel towards the second of the supply channel may be controlled by the pressure system as well as by the curtain control means, which monitors and controls the pressure differences (dP_mc, dP_s) in the system. As the sideways flow of the gaseous material towards the barrier gas curtain is highly one-directional, the gaseous material continuing to flow in the supply channel past the intersection, is still representative for the gaseous environment and not diluted by barrier gas, it may therefore be directed towards further analysis chambers and analyser systems.

In one or more embodiments, one or more further measurement channel may be arranged in connection to said supply channel between the measuring channel and the second end of the supply channel. Essentially, the further measuring channel may be arranged with any of the described arrangement, control means, sensors and units etc. of the gas analyser described in one or more embodiments herein. E.g. the further measuring channel may likewise be arranged with optical units for optical measurements or other instruments for different measurements of the gas material. It may furthermore be arranged with a further barrier gas arrangement for protecting the optical components or other sensitive components. Likewise, the barrier gas curtain and entrained gas material may be directed to a pressure tank, e.g. the same pressure tank as used with the measuring channel as described previously. The pressures within the further measuring channel may be controlled by a pressure systems, e.g. the pressures associated with measuring channel and further measuring channel may be controlled by the same pressure system.

In one or more embodiments, the nozzle may be arranged so that the barrier gas curtain is introduced in to the measuring channel in a direction substantially perpendicular to the longitudinal extend of the measuring channel.

Advantageously, with the flow direction being perpendicular to the longitudinal extend of the measuring channel is the shortest transverse extent across the channel, minimizing the requirements to the distance across which the barrier gas curtain has to extend. Furthermore, the flow can be easily directed toward the opposing barrier gas outlet opening, minimizing the risk of unwanted turbulence. In one or more embodiments, the gas curtain extends across substantially the entire transverse cross-section of said measuring channel. In one or more embodiments, the dimensions of the nozzle design are preferably configured to provide a thin and well defined barrier gas curtain.

In one or more embodiments, the longitudinal extent of the measuring channel is arranged along a second axis ($a2$), the transverse cross-section of the measuring channel is defined by a first ($a1$) and third axis ($a3$), being perpendicular to one another, and to said second axis ($a2$).

In one or more embodiments, the barrier gas outlet opening may be of a width (Wo) measured along the longitudinal extend of the barrier gas outlet opening which is at least equal or larger than the width of the nozzle opening (Wn), measured perpendicular to the longitudinal extend of the measuring channel.

In one or more embodiments, the barrier gas outlet opening may be of a length (Lo), measured perpendicular to the longitudinal extent of the barrier gas outlet opening, which is at least equal or larger than the length of the nozzle opening (Ln), wherein the length is measured parallel to the longitudinal extent of the measuring channel.

The nozzle opening and the barrier gas outlet opening may preferably be shaped as elongated openings, such as slot openings, which has a width (Wo, Wn) larger than the length (Lo, Ln) of the openings. The lengths (Lo, Ln) of the openings are measured along the second axis ($a2$), such as perpendicular to the longitudinal extent of the nozzle opening and barrier gas outlet opening, while the widths (Wo, Wn) of the openings may be substantially measured along third axis ($a3$) such as along the longitudinal extend of the nozzle opening and barrier gas outlet opening. By providing an outlet opening width (Wo) which is at least equal but preferably larger than the nozzle opening width (Wn), it is ensured that all of the barrier gas introduced in said measuring channel is removed again, even at different flow rates of the barrier gas curtain, without creating undesired turbulence. Preferably, the barrier gas outlet is arranged to collect all of the barrier gas introduced by the opposing barrier gas inlet from the measuring channel.

In one or more embodiments the length (Ln) of the nozzle opening is between 0.1 and 2 mm, such as between 0.3 and 1.5 mm, preferably between 0.5-1 mm. The length (Lo) of the barrier gas outlet opening is between 1 and 10 mm, such as between 2.5 and 8.5 mm, preferably between 3.5-5 mm. In one or more embodiments the length (Lo) of the barrier gas outlet opening is 3-7 times larger than the length (Ln) of the nozzle opening, such as approximately 4-6 times larger, such as preferably 5 times larger than the length of the nozzle opening.

In one or more embodiments, the width (Wn) of the nozzle opening or the width (Wo) of the barrier gas outlet opening, or both, may preferably be at least 1-3 times larger, such as 1.5-2 times larger than the maximum width of the measuring channel. In one or more embodiments, the width (Wn) of the nozzle is between 10-100 mm, such as between 40-80 mm, preferably between 50-70 mm.

In one or more embodiments, the nozzle may comprise an array of one or more openings, through which barrier gas is introduced into said measuring channel. The total width of the array of openings may be of the same width as the width (Wn) of the nozzle opening as described above. The total length of the array of openings may be of the same length as the length (Ln) of the nozzle opening as described above. In one or more embodiments, the barrier gas outlet is arranged to collect the entire amount of gaseous material in the vicinity of said barrier gas outlet opening.

In one or more embodiments, the centre-point of the nozzle opening and the centre-point of the barrier gas outlet opening may be displaced at a distance (d_tilt) relative to each other along the longitudinal extent of the measuring channel.

Preferably, the centre-point is defined as the point in the centre of the opening. Each opening may be defined as enclosed by an edge. In one or more embodiments, at least a part of the edge of the nozzle opening is opposing at least a part of the edge of the barrier gas outlet opening. The opposing parts of the edges may be arranged directly adjacent to the optical window of the optical unit, such that the edges are aligned along a line being perpendicular to the longitudinal extend of the measuring channel. In one or more embodiments the opposing parts of the edges may be aligned along a line being parallel with the first axis (a1) and or the optical window. This advantageously provides a barrier gas curtain which undergoes more expansion towards the intersection and the gaseous material in the measuring channel, than towards the optical window.

In one or more embodiments the barrier gas curtain is provided directly adjacent to the optical window, such as abutting the optical window. This advantageously provides a barrier gas curtain which may be utilized for cleaning the optical surface and not only for isolating it from the gaseous material. The barrier gas curtain may mainly comprise a substantially straight flow of barrier gas portion being adjacent to the optical window.

In one or more embodiments, the nozzle opening is preferably smaller in extend than the barrier gas outlet opening, such that the edge of the nozzle opening towards the intersection between the measuring channel and the supply channel extends further toward said intersection than the nozzle opening edge towards said intersection. This advantageously provides a setup, where the barrier gas outlet opening is able to accommodate both the barrier gas but also the gaseous material entrained.

In one or more embodiments, the optical units may be arranged to provide a beam of electromagnetic radiation through said measuring channel, and wherein the barrier gas curtain is of a thickness (T_bg), being between 0.5-8 mm, such as between 1-6 mm, preferably between 2-4 mm, measured along a centreline of said electromagnetic beam.

The beam of electromagnetic light may be generated by a laser, such as an IR-laser, but it may be any light source, such as white light, from the visible light spectrum, or ultraviolet light. The centreline may be defined as line extending through the centre of the beam along the propagation direction of beam. The thickness of the barrier gas curtain where the centreline of the beam intersects the barrier curtain is an important size to know in order to be able to accurately calculate the distance travelled by the beam through the gaseous material which is analysed. Advantageously, the barrier gas curtain provides well-defined and thin barriers, making the gas analysis more accurate.

In one or more embodiments, the optical units may be arranged to provide a beam of electromagnetic radiation through said measuring channel, and wherein the barrier gas curtain is of a thickness (T_bg) extending over a isolation distance (d_isolation) making up between 0.1-2.0%, such as 0.2-1.0% of the total distance (d_total) that the beam travels through in the measuring channel.

Preferably, a subtraction of the isolation distance from the total distance equals the testing distance (d_test), corresponding to the distance along which the beam interacts with gaseous material, and used for the calculations in the gas analysis. Advantageously, the thin barriers only extend over a small fraction of the total distance travelled by the beam, allowing for a large percentage of the total distance to be utilized for gas analysis measurements, providing an optimized and more accurate gas analyser system.

The first end of the supply channel may open into the gaseous environment, such as flue gas or combustion gas within a chimney. In one or more embodiments, the supply channel may open into the gaseous environment via a probe channel and a probe arrangement comprising one or more filters.

In one or more embodiments, the gas analyser system further comprises a probe arrangement for collecting said gaseous material from a gaseous environment, wherein the probe arrangement is in connection with said supply channel, and wherein the probe arrangement is equipped with one or more filter arrangement(s) arranged to filter said gaseous material prior to entering the supply channel.

For optical measurements, a sample from a gaseous environment of high dust content can prove to be inefficient and difficult to analyse as only a small fraction of the light beam reaches the receiver. Preferably the one or more filters are configured to separate dust from the gaseous material at a high flow rate. The gaseous material is preferably extracted from said gaseous environment through the filter(s) and into said supply chain due to the pressure difference (dP_s), provided by the pressure system, generating suction through supply channel. In one or more embodiments the first pressure (P1) may be measured at the probe arrangement, such as near the filter facing the gaseous environment. Advantageously, as the gas is extracted due to the internal pressure difference (dP_s) of the gas analyser system, the flow rate of extracted gaseous material can be precisely controlled and modulated by the pressure system. Preferably the gas material flow rate through the probe arrangement and the supply channel is independent of the flow rate of gaseous material in the gaseous environment.

In one or more embodiments, the gas analyser system comprises a cleaning device for cleaning said filter arrangement from particulates and dust, wherein the cleaning device is in connection with an air source and configured to provide a portion of cleaning air, preferably a pulse of cleaning air out through at least the filter arrangement to the gaseous environment.

In one or more embodiments, the cleaning device may additionally or alternatively be provided with a gas source, such as a nitrogen gas source for cleaning said filter arrangement. Advantageously, the cleaning device makes it possible to clean the filter arrangement without the need manually clean the filter arrangement.

In one or more embodiments, the pressure system may be configured to detect a pressure drop across the filter arrangement, which may indicate that the filter arrangement needs to be cleaned. The gas analyser may comprise a cleaning device control unit configured to activate the cleaning device once a threshold pressure drop is detected by the pressure system. The pressure system may be provided with a pressor sensor to detect such pressor drop and to provide an output accordingly to the cleaning device control unit. Upon activating of the cleaning device, the pressure difference (dP_s) within the supply channel may be reduced or set temporarily to zero or above.

In one or more embodiments, the supply channel may be connected to said probe arrangement through a probe channel, wherein the supply channel is arranged at a substantially 90 degree angle to the probe channel. Preferably the supply channel is connected to said probe channel between at a location along the probe channel between said cleaning arrangement and said filter arrangement. The cleaning gas may then be directed along a straight channel to said probe channel and out through said filter arrangement, by-passing the supply channel.

In one or more embodiments, the gas analyser system comprises a calibration arrangement for filling said measuring channel with calibration gas, wherein the calibration arrangement has one or more calibration gas inlet arranged in connection with said supply channel between said first end of the supply channel and said measuring channel.

Advantageously the calibration gas may be sucked through the system in the same manner as the gaseous material during operation of the gas analyser system, i.e. it may be directed through the supply channel and the measuring channel by the pressure difference (dP_S) and negative pressure created at the barrier gas curtain. In one or more embodiments, the probe arrangement may comprise a shutter arrangement which is arranged to be able to close the fluid connection between said supply channel and said gaseous environment, so that gaseous material is not directed through the gas analyser during calibration.

The gaseous environment may be a hostile environment containing species which may etch and/or damage optical surfaces, such as corrosive adhering gasses. Condensation of water vapour is undesirable in gas analyser systems because, in combination with some species in the gases from the gaseous environment, it may form corrosive sulfuric and nitric acids. In order to prevent condensation of the corrosive acids, it is preferred that the temperature of inner surfaces of the gas analyser system is kept at a temperature being larger than the acid dew-point.

In one or more embodiments, the probe arrangement comprises probe heating means for heating at least parts of said probe arrangement, such as the filter arrangement.

The probe heating means may be arranged to heat the filter arrangement and any channels extending from the filter arrangement to the supply channel, so as to avoid reaching the acid-dew point.

In one or more embodiments, the gas analyser system comprises channel heating means for heating said gaseous material in said supply channel and/or said measuring channel or both, and wherein the channel heating means comprises a channel heat controller for controlling said temperature in said channel(s).

Preferably the heating means are arranged to be able to heat at least the interior surfaces of the gas analyser system, which may come into contact with the gaseous material, so as to avoid condensation.

In one or more embodiments, the gas analyser system comprises barrier gas heating means for heating said barrier gas curtain, wherein the barrier gas heating means comprises a barrier gas heat controller for controlling said temperature of said barrier gas curtain.

The barrier gas heating means may be arranged to maintain the temperature of the barrier gas curtain above temperature sufficient to avoid condensation species of the gaseous material. The heating means may be any suitable heating means such as electrical heating means.

In one or more embodiments, the gas analyser system comprises one or more temperature sensor(s) for detecting a temperature within said gas analyser and provide an output accordingly.

Advantageously, the temperature sensors allows monitoring and detecting the temperature throughout the system and furthermore allows for rapid detection of any sudden temperature change which may be disadvantageous for the gas analysis, whereby the operator or control system may swiftly compensate for such temperature change by activating or deactivating one or more of the heating means.

One or more temperature sensors may be arranged in connection to said supply channel so as to measure the temperature in said supply channel and so as to provide an output accordingly to said channel heat controller. In one or more embodiments, further temperature sensor(s) may be arranged to measure the temperature within the measuring channel, and provide an output accordingly to the channel heat controller. The channel heating means may be arranged to adjust said thermal energy provided to said channels based on said outputs.

Additionally or alternatively, the probe heating means may comprise one or more temperature sensor to measure the temperature at the probe arrangement and provide an output accordingly to a probe heat controller comprised in said probe heating means for controlling said temperature based on the output.

In one or more embodiments, the gas analyser system comprises one or more temperature sensor(s) in connection to said barrier arrangement, preferably near said barrier gas inlet, so as to measure the temperature near said barrier arrangement and so as to provide an output accordingly to said barrier gas heat controller.

In one or more embodiments, the temperature sensor(s) within the gas analyser system may be set to continuously detect the temperature and provide outputs(s) accordingly, allowing for continuous monitoring and adjustment of the temperatures throughout the gas analyser system. In one or more embodiments, the heat controller(s) of the gas analyser system may be configured to automatically adjust the temperature, by activating said heating means based on received outputs from the pressure sensors. Alternatively or additionally the heat controllers may be arranged to provide a constant temperature within a pre-set range of temperatures.

Advantageously, by heating one or more sections of the gas analyser system, the function and durability of the gas analyser system may independent on any temperature changes in the gaseous environment, since the gas analyser system may be arranged to compensate for any temperature changes by e.g. providing additional heating if that is desired, e.g. in order to avoid the dew point, or may adjust the provided thermal heating of by the heating means, so as to match the temperature of the gaseous material as it enters the gas analyser system. This is especially advantageous if it is a desire to measure the gas material in its original condition and state.

The second aspect of the present invention relates to a method for measuring a gaseous medium in a gas analyser system, wherein the gas analyser system comprises
  a supply channel having an inlet supply opening at a first end near a gaseous environment containing said gaseous medium, and one or more outlet supply opening(s) at a second end of the channel, and
  a measuring channel connected to said supply channel between said first and second end, an analysing unit, comprising an optical arrangement for analysing said gaseous material contained in said measuring channel, wherein the optical arrangement comprises a first optical unit arranged at a first end of the measuring channel and a second optical unit arranged at a second end of said measuring channel, a barrier arrangement arranged near each end of the measuring channel comprising a barrier gas inlet and a barrier gas outlet arranged in opposing manner across said measuring channel, each barrier gas inlet is in connection with an gas source, such as an air source, and provided with a nozzle having a nozzle opening being directed towards said opposing barrier gas outlet having a barrier gas outlet opening, wherein the method comprises the steps of providing a pressure difference (dP_s) between the pressure of the gaseous material at said inlet supply opening and said outlet supply opening, so as to force gaseous medium from said supply inlet opening toward said supply outlet opening, providing a flow of barrier gas through said nozzle opening toward said barrier gas outlet opening, so as to provide a barrier gas curtain and so as to force at least a part of said gaseous material from said supply channel into said measuring channel, towards said barrier gas curtain, and measuring said gaseous material in said measuring channel using said optical arrangement.

In a preferred embodiment, the supply channel directs gaseous material from the inlet opening to the outlet opening of the supply channel, on the way towards the supply opening the gaseous material will be affected by a draft. The gaseous material will be forced sideways, filling the measuring channel with gaseous material. This sideways suction of gaseous material is preferably provided by the barrier gas curtain, which is of a high-velocity curtain extending across the measuring channel. As the barrier gas curtain enters the measuring channel, where the measuring channel is kept at a pressure lower than the pressure of the gas curtain, the curtain will expand providing a low pressure zone relative to the pressure in the supply channel and thereby cause a pressure gradient from the supply channel to the barrier gas curtain.

In one or more embodiments, the pressures within the system may preferably be such that the pressure gradient in the supply channel, from the first end to the second end, is larger than the pressure gradient in the measuring channel, from the intersection between the measuring channel and the supply channel to the barrier gas curtain, whereby only a fraction A of the gaseous material is directed from said supply channel to said barrier gas curtain. The gaseous material is preferably distributed in the measuring channel and continuously replaced by new gaseous material while the optical measurements are taking place.

In one or more embodiments, the method further comprises the step of collecting said barrier gas and said gaseous material from said barrier outlet, and collecting said gaseous material from said supply outlet.

In one or more embodiments, the gas analyser system further comprises a pressure system and one or more pressor sensors for measuring and controlling pressures within said gas analyser system, wherein the method further comprises the step of measuring said pressure difference (dP_s) and provide a data output accordingly using said pressure system.

In one or more embodiments, the method further comprises the step of controlling said pressure difference (dP_s) based on said data output using said pressure system.

Preferably the pressure system is arranged to automatically adjust the pressure at the supply outlet opening so as to provide the desired pressure difference (dP_s). The pressure system may advantageously also be arranged to control other pressures within the gas analyser system, such as the pressure applied to the nozzle opening (P3).

In one or more embodiments, the pressure system comprises a first pressure sensor arranged to measure a first pressure (P1) of the gaseous material near the inlet supply opening and a second pressure sensor arranged to measure a second pressure (P2) of the gaseous material near the outlet supply opening, and provide a first data output and second data output accordingly and wherein said method comprises the step of calculating said pressure difference (dP_s) by subtracting the measured second pressure (P2) from the measured first pressure (P1).

In one or more embodiments, the pressure system comprises one or more pressure controller(s) arranged to control said second pressure (P2), and wherein the method comprises the step of controlling said pressure difference (dP_s) based on said data output by controlling said second pressure (P2) using the one or more pressure controller(s).

Advantageously, this allows for the pressure difference (dP_s) to be controlled to desired levels and to be adjusted in case of pressure drops in the gaseous environment. In one or more embodiments, the pressure difference (dP_s) (dP=P1−P2) is between minus 10-100 mbar, with the pressure at the supply outlet opening being lower than the pressure at the supply inlet opening.

In one or more embodiments, the pressure system comprises a one or more pressure controller(s) arranged to adjust said first pressure (P1) and second pressure (P2) of said gaseous material based on said data output.

In one or more embodiments, the method comprises the step of providing a barrier gas curtain from said barrier gas inlet to said barrier gas outlet, wherein the barrier gas curtain is of a width (W_bg) larger or equal to the width (W_mc) of the measuring channel.

The barrier gas curtain provided advantageously extends over the entire width of the measuring channel, so as to effectively separate the gaseous material from the optical units. In one or more embodiments, the barrier gas curtain also extends the entire distance from the nozzle opening to the barrier gas outlet opening.

In one or more embodiments, the method comprises the step of providing a barrier gas curtain from said barrier gas inlet to said barrier gas outlet which is of a barrier gas curtain thickness (T_bg) being between 1-10 mm.

The thickness of the barrier gas curtain is defined along the centreline of the optical electromagnetic beam, and may in one or more embodiments be preferably between 2-4 mm.

In one or more embodiments, the gas analyser system is a gas analyser system according to any of the claims 1-23.

In one or more embodiments, the gas analyser of the method according to the second aspect of the invention may comprise any of the features and advantages described in relation to the gas analyser according to the first aspect of the invention.

The present invention further relates to the use of a gas analyser system according to any of the claims 1-23 for analysing characteristics of a gaseous material, such as a flue gas.

DRAWINGS

Aspects of the present disclosure will be described in the following with reference to the figures in which.

DETAILED DESCRIPTION OF THE INVENTION

Figure 1:
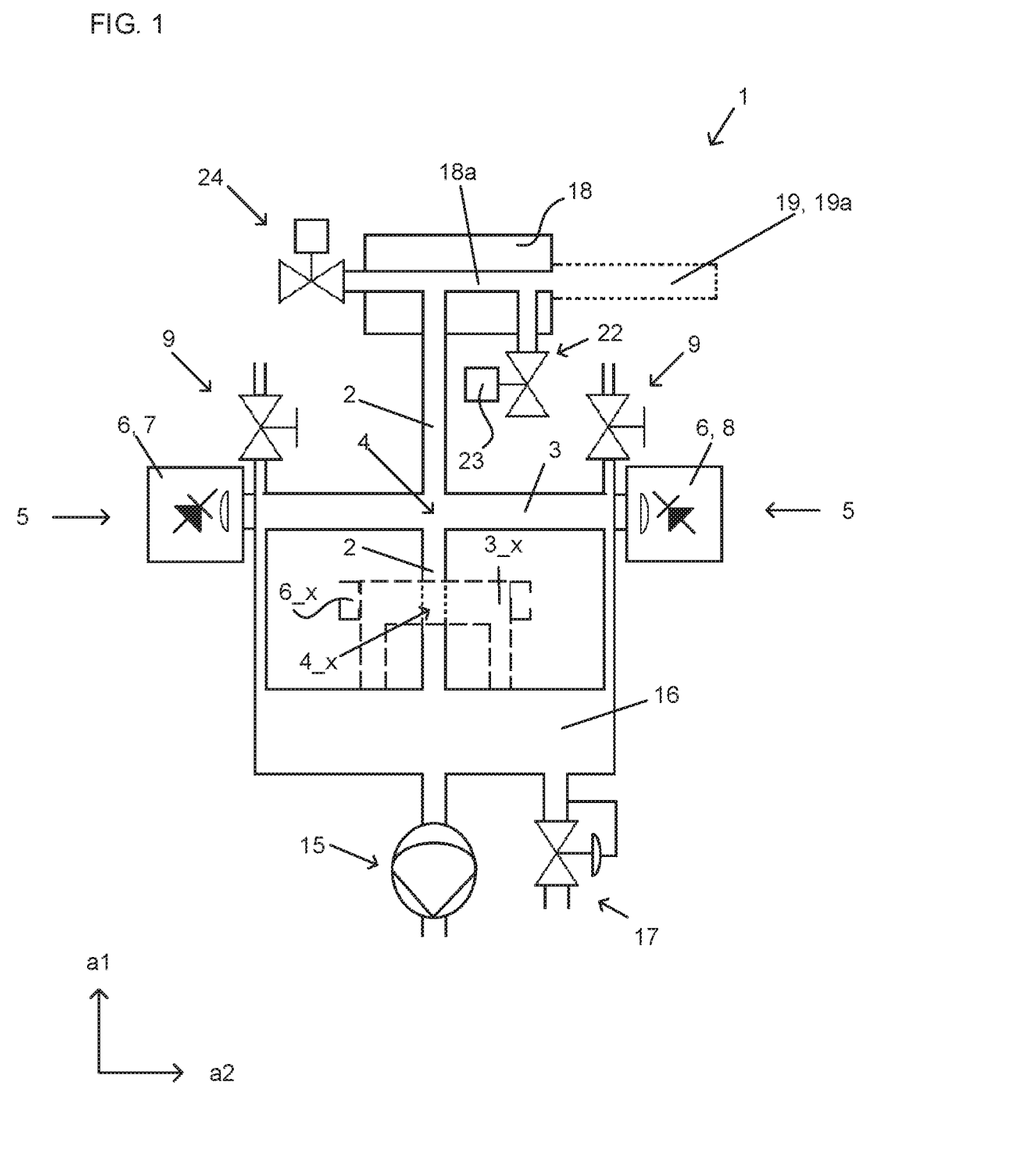
FIG. 1 shows a schematic drawing of a gas analyser according to an embodiment of the invention.

FIG. 1 illustrates a schematic drawing of an exemplary extractive gas analyser system 1 according to embodiments of the invention. The gas analyser system 1 can generally be considered as comprising three interconnected sections; a probe section, an analysis section, comprising an analysing unit 5, and a pressure section. The probe section is the part of the gas analyser system which allows gas material to be extracted from a gaseous environment, such as the gaseous environment present inside a chimney. The gas analyser may comprise one or more probe arrangement connected to the supply channel. In the present embodiment shown in FIG. 1, the probe section comprises a probe element extending into the gaseous environment and mounted with a filter arrangement for filtering the gaseous material from larger species such as dust and possible also other particulates. Extending from the probe element is a probe channel 18a, which is shown in connection with the supply channel 2, connecting the probe section with the analysis section and the pressure section.

In one or more embodiments and in the present exemplary gas analyser 1 between the filter arrangement 19 and the supply channel 2 a calibration arrangement 22 is shown connected to the probe channel 18a. The calibration arrangement 22 is for introducing a calibration gas of known content into the gas analyser system for calibration of the analysing unit 5. The calibration arrangement 22 comprises a calibration inlet to said probe channel 18a, a calibration gas source 23 and preferably also a control device for selectively activating, deactivating and adjusting the flow of calibration gas from the calibration arrangement 22. A flow meter may be utilized to monitor and adjust the calibration gas flow.

In one or more embodiments, and in the present example, a cleaning device is arranged in connection to said probe channel 18a, e.g. in extension to said probe channel 18a from said filter arrangement 19. The cleaning device is arranged to provide a flow of cleaning gas towards said probe arrangement 18, so as to clean one or more filters of said filter arrangement 19 by a blow-back process, where the cleaning gas is directed through the filter into the gaseous environment. The flow of cleaning gas may be one or more pulse of cleaning gas.

FIG. 1 further illustrates the supply channel 2, being connected to the aforementioned probe section at a first end of the supply channel 2 and from there extending to a measuring channel 3 being a part of the analysing unit 5. In the present example the measuring channel is connected to across in the supply channel 2 in a four-way intersection 4, providing three pathways for the gas material transported through the supply channel 2 from probe channel 18a. In the present example, an optical unit 7, 8 is arranged in each end of the elongated measuring channel 3. The measuring channel 3 can comprise two channel parts present on each side of the intersection 4, the first part nearest the end of the measuring channel is the isolation part, providing a gas wall between the optical unit 7, 8. The first optical unit 7 may comprise a transmitter for transmitting electromagnetic radiation and the second optical unit 8 may comprise a receiver for receiving said electromagnetic radiation after travelling through and interacting with the gas material. Alternatively, one of the optical units 7, 8 may comprise both the receiver and transmitter while the opposing optical unit 7, 8 comprises a mirror arrangement, reflecting the electromagnetic radiation. For the gas analysis the absorbance or the transmission spectrum may be obtained or both. The initial electromagnetic radiation transmitted may be originated from a laser arrangement producing electromagnetic radiation of a wavelength between 200-3000 nm, such as between 400-2500 nm, such as electromagnetic near-IR radiation or far-IR-radiation. Preferably, the isolation part has a controlled length, which is not considered in concentration calculations for the gas analysis. The remaining part of the measuring channel 3 nearest the intersection 4 is preferably the testing part of the channel where the gaseous material is analysed, each testing part being connected across the intersection 4. The length of the testing part, defines the length the electromagnetic radiation has travelled through gaseous material and is used in the calculation of gas analysis.

Figure 2:
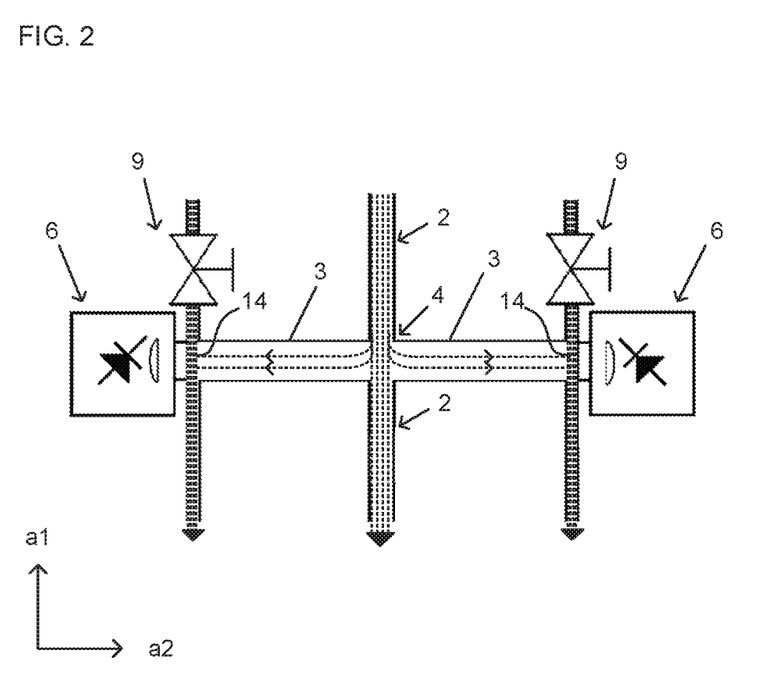
FIG. 2 shows a schematic drawing of a section near the analysing unit of a gas analyser according to an embodiment of the invention, shown with indications of direction of flow of the barrier gas and gaseous material.
Figure 3:
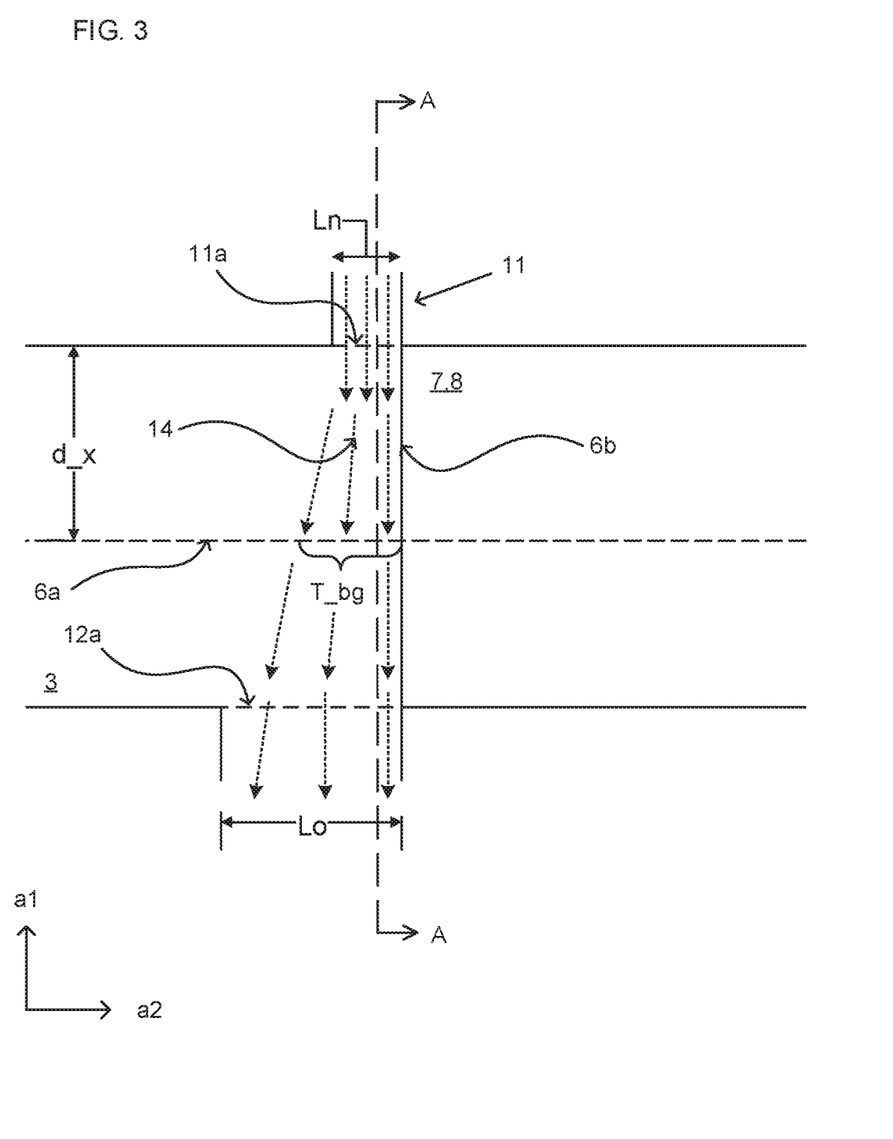
FIG. 3 shows a schematic cross-sectional side view of a measuring channel according to an embodiment of the invention with barrier gas curtain provided across the measuring channel.
Figure 4:
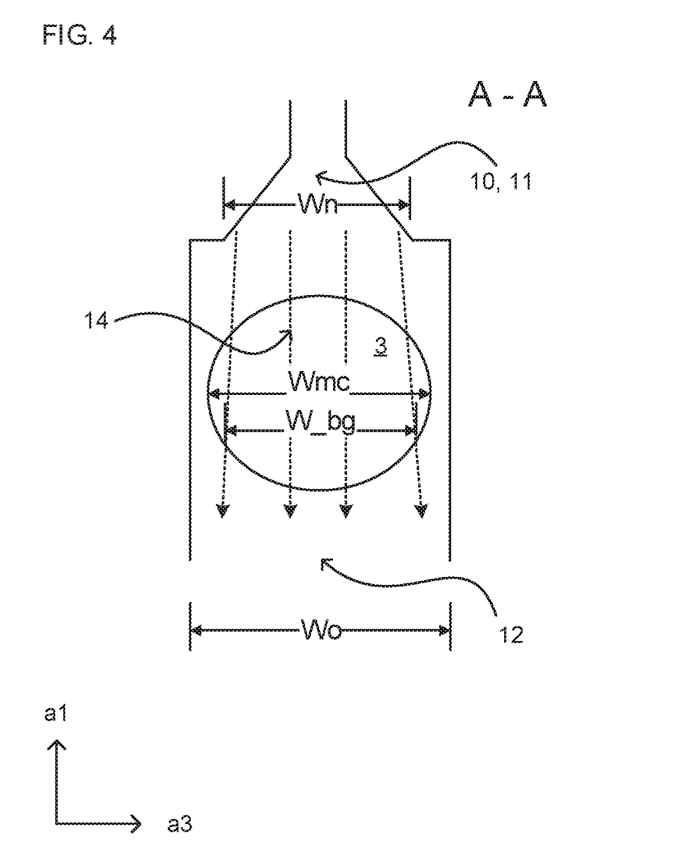
FIG. 4 shows a schematic cross-sectional front view of the measuring channel with a barrier gas curtain as shown in FIG. 3.

As shown in FIGS. 1-4, at each end of the measuring channel 3, a through-going pathway is arranged perpendicular to the longitudinal extend of the measuring channel 3. The measuring channel 3 is arranged so that the longitudinal extent of the measuring channel 3 is perpendicular to a first axis (a1), and third axis (a3) and parallel to a second axis (a3), with a transverse cross-section of the measuring channel 3 defined by a second axis (a1) and a third axis (a3). In one or more examples the first axis (a1) is orientated substantially vertical while the third axis (a3) and the second axis (a2) may be orientated substantially horizontal. In the present example barrier gas arrangements are arranged in the isolation part of the measuring channel 3 and the barrier gas arrangement are preferably identical at each end of the measuring channel 3. The physical setup of the analysing unit 5 may be mirrored in the intersection between the supply channel 2 and the measuring channel 3. The through-going pathway is a part of a barrier arrangement 9, and provided by a barrier gas inlet comprising a nozzle having a nozzle opening 11a providing the barrier inlet opening 10a to the interior of the measuring channel 3 and an opposing barrier gas outlet 12, having a barrier gas outlet opening 12a to the interior of the measuring channel 3. In one or more examples, the extent of the barrier gas outlet opening 12a is orientated perpendicular to the first axis (a1). The barrier arrangement further comprises a barrier gas source connected to said barrier gas inlet, which can provide a flow of barrier gas from the barrier gas inlet 10 to the barrier gas outlet 12, so as to create a barrier gas curtain 14 covering the distance between at least from the nozzle opening 11a to the barrier gas outlet opening 12a. In one or more examples, the gas of the barrier gas curtain 14 is directed along the first axis (a1). An example of the barrier gas curtain 14, preferably such as an air knife, is illustrated in FIGS. 2-4. The barrier gas curtain 14 may contain air or an inert gas such as nitrogen or argon. The opposing nozzle opening and outlet openings 11a, 12a are arranged in the isolation part of the measuring channel 3 between the supply channel 2 and the optical units 7, 8, so that the barrier gas curtain 14 provides a spatial separation of the optical units 7, 8 and the gas material introduced through the supply channel 2.

In one or more embodiments of the present invention, and as illustrated in FIG. 3-4, the barrier gas inlet 10 comprises an elongated nozzle, having a nozzle opening 11a of a width (Wn) and a length (Ln), designed to direct the barrier gas into a high-speed jet. Additionally, the nozzle may preferably be designed such that the width of the nozzle (Wn) is larger than the width (Wmc) of the measuring channel 3, measured along the third axis (a3) perpendicular to the first (a1) and second axis (a2) as illustrated in FIG. 4. This allows for a uniform barrier gas curtain 14 extending across the entire measuring channel 3. In one or more embodiments, the width of the nozzle (Wn) is approximately 1-2 times larger than the largest width (Wmc) of the measuring channel 3. In one or more embodiments the length (Ln) of the nozzle opening is between 0.5 and 1.0 mm. The length (Lmc) of the measuring channel 3 may be between 0.3 and 1.5 m, such as between 0.5 and 1 m long, measured along the second axis (a2). The width (Wmc) of the measuring channel 3 may be between 2 and 6 cm such as around 4 cm. In one or more examples, the measuring channel 3 may preferably be a cylinder of a diameter corresponding to said measuring channel width (Wmc).

In one or more embodiments, and as illustrated in FIG. 3 and FIG. 4, the barrier gas outlet 12 has an barrier gas outlet opening 12a which is of a length (Lo) being larger than the length (Ln) of the barrier gas inlet, measured along the second axis (a2). The barrier gas outlet length (Lo) is preferably of a length (Lo) of a size to allow for sufficient discharge of the mixed volume of gaseous material sucked towards the barrier gas curtain 14 and the barrier gas 14 itself, without causing unwanted turbulence near the edges of the barrier gas outlet opening 12a. In one or more examples, the barrier gas outlet opening length (Lo) is between 5 to 10 times larger than the largest length of the nozzle opening (Ln). In one or more examples, the length of the outlet opening (Lo) is between 4-5 mm, such as approximately 4.5 mm.

The barrier arrangement 9 is preferably configured to provide a flow of barrier gas across the measuring channel 3 due to the presence of a pressure gradient. The barrier gas is compressed to a pressure of e.g. 1-5 bar, such as 2-4 bar or such as 3 bar and creating a jet flow of barrier gas when exiting through the nozzle e.g. at a flow rate of about 1-3 litres/minute, thereby providing the barrier gas curtain 14. The design of the nozzle 11 provides a thin well-defined barrier gas curtain 14. The barrier gas curtain 14 is preferably a pressurized air plenum exiting through the elongated nozzle opening or slot in a laminar (uniform) flow pattern. As illustrated in FIGS. 3-4, as soon as the barrier gas leaves the nozzle, it expands as the surrounding gas in the measuring channel 3 is kept at a lower pressure. The expansion creates an advantageous low pressure near the curtain 14 relative to pressure in the stream of gaseous material from the supply stream through the supply channel 2, whereby the gaseous medium is forced sideways into the measuring channel 3, through the testing part and subsequently entrained by the air curtain stream 14, as shown by the arrows in FIG. 2. The barrier gas curtain preferably provides at least an additional draft in the measuring channel.

The barrier gas curtain is of a thickness (T_bg) measured along the along centreline of the electromagnetic radiation 6a, e.g. which preferably propagates parallel to the second axis (a2), and further be of a width (W_bg) measured along the third axis (a3) as illustrated in FIG. 4. In one or more examples, the thickness (T_bg) of the barrier gas curtain 14, may be adjusted by the adjusting the flow rate of barrier gas from the nozzle 11 towards the barrier gas outlet 12. In one or more embodiments, the flow rate through the nozzle 11 may be controlled based on measurements by a flowmeter arranged near the barrier gas inlet 10. As the barrier gas exits the nozzle opening 11a and enters the measuring channel 3, the barrier gas curtain 14 expands. The thickness (T_bg) of the curtain is preferably adjusted to be approximately between 2-4 mm, measured approximately along the intersection between the centre-line of the electromagnetic radiation 6a from the optical arrangement and the barrier gas curtain 14, as illustrated in FIG. 3. The centre line of the electromagnetic radiation 6a may approximately be located at a distance (d_x) from the nozzle opening 11a, along a line from the nozzle 11 to the outlet opening 12 e.g. corresponding to half of the measuring channel width (Wmc).

In one or more embodiments, the optical units 7, 8 each comprise an optical window 6b, of an optical transparent material, facing the interior of the measuring channel and preferably separating the interior components of the optical units 7, 8 from the gases in the measuring channel 3. As illustrated in FIG. 4 is it possible for the barrier gas curtain 14 to undergo a change in width (W_bg) across the measuring channel 3 due to the expansion of the barrier gas curtain 14, creating an increase in width (W_bg) of the barrier gas curtain 14 from the nozzle opening 11a to the outlet opening 12a as shown in FIG. 4. FIG. 4 is a cross-sectional view along the line A-A of the barrier arrangement 9 shown in FIG. 3.

The centre of the barrier gas outlet opening 12a and the centre of the nozzle opening 11a may be aligned on a same line extending through the centre's and parallel to the first axis (a1). In one or more examples and as shown in FIG. 3 the barrier arrangement 9 the barrier gas outlet 12 and barrier gas inlet 10 alignment is such that, the centre of the nozzle opening 11a is not arranged on a line extending perpendicular from the centre of the barrier gas outlet opening 12a and parallel to the first axis (a1), but the centre of the nozzle opening 11a is instead positioned at a displacement distance measured along the second axis (a2). Furthermore, in the present example the optical window 6b is arranged directly adjacent said barrier gas curtain 14, preferably with the surface of the optical window 6b, facing the curtain 14. The optical window 6b may additionally be connected to edges of the nozzle opening 11a and barrier gas outlet opening 12a so as to minimize any flow obstacles which may cause turbulence when the barrier gas curtain 14 is generates and flows. At least a part of the edges of the nozzle opening 11a and the barrier outlet opening 12a directly adjacent to the optical window 6b, may be directly aligned on the same line across the channel 3, perpendicular to the first axis (a1), but the barrier gas outlet opening 12a is in the present example larger and therefore extending further along the second axis (a2) away from the optical window 6b. The larger outlet opening 12a allows for efficient collection of both the barrier gas but also the entrained gaseous material. Due to an efficient control of the pressure within the gas analyser system 1, the barrier gas curtain 14 thickness (T_bg) and amount of entrained gas can be efficiently controlled, significantly reducing the risk of damaging or contaminating the optical windows 6*b*.

In one or more embodiments, approximately 20-30% of the gaseous material entering the measuring channel 3 is directed sideways by the barrier gas curtain, while the remaining 70-80% of the gas material continuous to flow through the supply channel 2, as illustrated in FIG. 2. The transverse draft, forcing a portion of the gaseous material to distribute in said measuring channel, can be increased or decreased by changing the flow rate of barrier gas through the nozzle opening 11*a*.

In one or more embodiments, and as an example shown in FIG. 1, the second end of the supply channel 2 is connected to a pressure tank 16, furthermore the barrier gas outlets 12 are also connected to the same pressure tank 16. This pressure tank 16 is kept at a second pressure (P2) being lower than a first pressure (P1) measured at the first end of the supply channel 2. This difference in pressures, generates a pressure difference (dP_s) and thereby a pressure gradient in the gas analyser system 1, which continuously forces the gaseous material from the gaseous environment through the system 1, such as from a the probe arrangement 18 through the probe channel 18*a*, through the supply channel 2 and to the pressure tank 16. The pressure in the pressure tank is controlled by a pressure control valve 17, such that the pressure difference (dP_s) is kept substantially constant, e.g. such that the second pressure (P2) is lower than the first pressure (P1) by approximately 30 mbar. In one or more embodiments, the pressure difference (dP_s) is controlled so as to generate a flow of gaseous material through the supply channel 2 of approximately 15 litres/minutes prior to the gaseous medium reaches the measuring channel 3, at which point parts of the gaseous material volume is forced sideways towards the barrier gas curtain 14 due to a high flow of barrier gas through the nozzle opening 11*a*.

The pressure tank 16, and the pressure control valve 17, is a part of a pressure system 15 which comprises further comprises one or more pressure sensors distributed in the system and displaying said measured pressure values and/or communicating the measured pressure values to a control unit of the pressure system 15. In one or more examples, a first pressure sensor may preferably be arranged in the supply channel 2 prior to the measuring channel 3 and arranged to measure a first pressure P1 and provide a data output accordingly. A second pressure sensor may be arranged in connection with the pressure tank 16 and measure the pressure within the tank 16, defined as the second pressure P2 and provide an output accordingly. When a difference exist between the first and second pressure, a pressure gradient is created forcing gaseous material from the first end of the supply channel 2, to the intersection between the supply channel 2 and the measuring channel 3 and towards the pressure tank 16. The pressure system 15 may preferably be arranged to control the pressure difference (dp_s) in response to the measured first pressure (P1) measured at first end of supply channel, by adjusting the second pressure (P2) by using the pressure control valve 17. The pressure system 15 may also be arranged to monitor and control the pressure of the barrier gas, defined as the third pressure (P3), in response to a pressure measurement device or sensor arranged to measure the barrier gas pressure (P3) prior to being discharged through the nozzle opening 11*a*. In one or more examples, as the second pressure (P2) is kept below the first pressure (P1) and as the pressure of the gaseous material is generally much less than the third pressure (P3) of the barrier gas, the second pressure (P2) will also be less than the barrier gas pressure (P3) thereby providing suction to the barrier gas outlet opening 12*a*.

The gas analyser system 1 according to embodiments of the invention is preferably arranged to utilize the high amount of barrier gas reaching the pressure tank 16 to dilute the gaseous material entering the pressure tank 16 from the second end of the supply channel 2. Du to this dilution of the gaseous material the pressure system components can be protected and no additional filtering or processing of the gas is needed. Preferably the mixture of gas in the pressure tank 16 contains a ratio between 1:30 to 1:70 of gaseous material to barrier gas, or of at least 1:50 of gaseous material to barrier gas.

In one or more embodiments of the present invention, in events that the filter(s) of the filter arrangement are extensively covered by dust or other blocking particulates, a drop in pressure near the first end of the supply channel 2, e.g. in the supply channel 2 nearest the probe arrangement 18 or in the probe channel 18*a*, will occur, which is detected by the pressure system 15. As a response to such pressure reduction, the aforementioned cleaning device 24 will be activated, and the filter arrangement 19 is cleaned.

In one or more embodiments, the supply channel 2 and the measuring channel 3 is preferably heated by a heating arrangement 20 comprising heating means 21*a*, 21*b*, such as electrical heating means. Furthermore, the barrier gas curtain 14 and/or the probe arrangement 18 and probe channel 18*a* may also be heated. Preferably the entire flow path for the gaseous material in the gas analyser system 1 is heated. The collected gaseous medium by the probe arrangement 18 may be of a high temperature, and furthermore contain species which may be harmful to the gas analyser system 1 if they are allowed to adhere to inner surfaces of the system 1. If the inner surfaces are colder than the gaseous material, condensation occurs due to the temperature difference and species are deposited to the surfaces. Therefore the heating means are preferably arranged to maintain the temperature of the inner surfaces and the barrier gas substantially equal to the temperature of the gaseous material throughout the probe section and analysing unit 5. In one or more examples, a number of temperature sensors are distributed in said gas analyser system 1 so as to monitor and detect any temperature difference between the gaseous material and the inner surfaces throughout the system 1. E.g. a temperature sensor may be arranged to measure the temperature at different positions scattered long the inner surface of the supply channel 2. A temperature sensor may also be arranged in said probe arrangement 18 and also near said barrier gas outlet 12 e.g. such as in a channel connection between said outlet opening 12*a* and the pressure tank 16. In one or more examples, a temperature control system may be comprised in said gas analyser system 1 for controlling the temperatures provided by the heating means based on outputs from the temperature sensors.

The gas analyser system 1 of the present invention may allow for several units 5 to be arranged in succession along the supply channel 2. In FIG. 1 a further measuring channel 3_x is schematically illustrated by dashed lines. The center-flow of gaseous material maintained in the supply channel 2 and continuing straight towards the second end of the supply channel 2 can be utilized for further gas analysis by connecting further measuring channels 3_x to said supply channel 2, e.g. by providing a further four-way intersection 4_x. These further measuring channels 3_x can furthermore be arranged with further optical arrangements 6_x (not shown) and further barrier arrangements. Essentially the further analysis section 5 may operate and be controlled in essentially the same way as the analysis section described in relation to the previous examples.

LIST OF REFERENCES

1 Gas analyser system
2 Supply channel
3 Measuring channel
3_x Further measuring channel
4 Four-channel intersection
4_x Further four-channel intersection
5 Analysing unit
6 Optical arrangement
6a Centre line of the electromagnetic radiation
6b Optical window
6_x Further optical arrangement
7 First optical unit
8 Second optical unit
9 Barrier arrangement
10 Barrier gas inlet
11 Nozzle
11a Nozzle opening
12 Barrier gas outlet
12a Barrier gas outlet opening
14 Barrier gas curtain e.g. air knife
15 Pressure system
16 Pressure tank
17 Pressure controller e.g. valve
18 Probe arrangement
18a Probe channel
19 Filter arrangement
19a Filter
22 Calibration arrangement
23 Calibration gas source
24 Cleaning device
a1 First axis
a2 Second axis
a3 Third axis
Lo Length of the barrier gas outlet opening
Ln Length of the nozzle opening
Lmc Length of the measuring channel
Wo Width of the barrier gas outlet opening
Wn Width of the nozzle opening
Wmc Width of the measuring channel
T_bg Thickness of the barrier gas curtain
P1 First pressure
P2 Second pressure
P3 Third pressure
dP_mc Pressure difference along the measuring channel
dP_s Pressure difference, dP_s=P2−P1
d_x distance between nozzle opening and the centre-line of the electromagnetic radiation.

The invention claimed is:
1. A gas analyser system for extractive measurement of a gaseous material, wherein the gas analyser system comprises:
a supply channel having an inlet supply opening at a first end and an outlet supply opening at a second end of the supply channel;
a measuring channel, comprising a first end and a second end, wherein the measuring channel is connected to the supply channel between the first end and the second end of the supply channel, and wherein the measuring channel is connected across the supply channel in at least a four-way intersection, providing at least three pathways for the gaseous material transported through the supply channel from the first end of the supply channel;
a pressure system, wherein the pressure system is arranged to provide a pressure difference, defined as a difference between a first pressure near the first end of the supply channel and a second pressure near the second end of the supply channel, wherein the first pressure is larger than the second pressure;
an analysing unit, comprising an optical arrangement for analysing the gaseous material contained in the measuring channel, wherein the optical arrangement comprises a first optical unit arranged at the first end of the measuring channel and a second optical unit arranged at the second end of the measuring channel, and wherein an optical measurement path is defined between the first optical unit and the second optical unit; and
a barrier arrangement arranged near each end of the measuring channel, each barrier arrangement comprising:
a gas source for providing a barrier gas; and
a barrier gas inlet and a barrier gas outlet arranged in opposing manner across the measuring channel, the barrier gas inlet is in connection with the gas source and provided with a nozzle having a nozzle opening being directed towards the opposing barrier gas outlet having a barrier gas outlet opening,
wherein the barrier arrangement is arranged to provide pressurized gas creating a barrier gas curtain between the barrier gas inlet and the barrier gas outlet hereby providing an area of low pressure so as to force least a part of the gaseous material from the supply channel into the measuring channel and entrained by the barrier gas curtain and discharged with the barrier gas curtain through the barrier gas outlet and so as to separate the gaseous material from the first and second optical units, such that the optical measurement path passes through the barrier gas curtain, and
wherein the barrier arrangement comprises a curtain controller for controlling a flow rate of the barrier gas curtain, and thereby controlling an amount of the gaseous material forced towards the barrier gas curtain.

2. The gas analyser system according to claim 1, wherein the gas analyser system comprises a first pressure sensor arranged near the first end of the supply channel so as to measure the first pressure and provide a data output accordingly to the pressure system.

3. The gas analyser system according to claim 1, wherein the gas analyser system comprises a second pressure sensor arranged near the second end of the supply channel so as to measure the second pressure and provide a data output accordingly to the pressure system.

4. The gas analyser system according to claim 1, wherein the gas analyser system comprises a control unit having a first pressure controller for controlling the second pressure based on a first data output and a second data output, preferably so as to maintain the pressure difference substantially constant or within a predetermined range.

5. The gas analyser system according to claim 1, wherein the pressure system comprises a pressure tank in connection to the outlet supply opening, and wherein the pressure tank is arranged to provide the second pressure to the outlet supply opening by a pump.

6. The gas analyser system according to claim 1, wherein the nozzle is arranged so that the barrier gas curtain is introduced into the measuring channel in a direction substantially perpendicular to a longitudinal extent.

7. The gas analyser system according to claim 1, wherein the barrier gas outlet opening is of a width, measured along a longitudinal extent of the barrier gas outlet opening, which is at least equal or larger than a width of the nozzle opening, measured perpendicular to a longitudinal extent of the measuring channel.

8. The gas analyser system according to claim 1, wherein the barrier gas outlet opening is of a length, measured perpendicular to a longitudinal extent of the barrier gas outlet opening, which is at least equal or larger than a length of the nozzle opening, measured parallel to a longitudinal extent of the measuring channel.

9. The gas analyser system according to claim 1, wherein a centre-point of the nozzle opening and a centre-point of the barrier gas outlet opening are displaced at a distance relative to each other along a longitudinal extent of the measuring channel.

10. The gas analyser system according to claim 1, wherein the first and second optical units are arranged to provide a beam of electromagnetic radiation through the measuring channel, and wherein the barrier gas curtain is of a thickness, being between 0.5-8 mm, such as between 1-6 mm, preferably between 2-4 mm, measured along a centreline of the beam of electromagnetic radiation.

11. The gas analyser system according to claim 1, wherein the first and second optical units are arranged to provide a beam of electromagnetic radiation through the measuring channel, and wherein the barrier gas curtain is of a thickness extending over an isolation distance making up between 0.1-2.0%, such as 0.2-1.0% of a total distance that the beam of electromagnetic radiation travels through in the measuring channel.

12. The gas analyser system according to claim 1, further comprising a probe arrangement for collecting the gaseous material from a gaseous environment, wherein the probe arrangement is in connection with the supply channel, and wherein the probe arrangement is equipped with a filter arrangement arranged to filter the gaseous material prior to entering the supply channel.

13. The gas analyser system according to claim 1, further comprising a barrier gas heater for heating the barrier gas curtain, wherein the barrier gas heater comprises a barrier gas heat controller for controlling a temperature of the barrier gas curtain.

14. The gas analyser system according to claim 1, further comprising a temperature sensor for detecting a temperature within the gas analyser system and providing an output accordingly.

15. A method for measuring a gaseous medium in a gas analyser system, wherein the gas analyser system comprises:
- a supply channel having an inlet supply opening at a first end of the supply channel near a gaseous environment containing the gaseous medium, and an outlet supply opening at a second end of the supply channel;
- a measuring channel, comprising a first end and a second end, wherein the measuring channel is connected to the supply channel between the first end and the second end of the supply channel, and wherein the measuring channel is connected across the supply channel in at least a four-way intersection, providing at least three pathways for the gaseous medium transported through the supply channel from the first end of the supply channel;
- a pressure system, wherein the pressure system is arranged to provide a pressure difference between a first pressure near the inlet supply opening and a second pressure near the outlet supply opening, wherein the first pressure is larger than the second pressure;
- an analysing unit, comprising an optical arrangement for analysing the gaseous medium contained in the measuring channel, wherein the optical arrangement comprises a first optical unit arranged at the first end of the measuring channel and a second optical unit arranged at the second end of the measuring channel, and wherein an optical measurement path is defined between the first optical unit and the second optical unit; and
- a barrier arrangement arranged near each end of the measuring channel, each barrier arrangement comprising:
- a gas source for providing a barrier gas; and
- a barrier gas inlet and a barrier gas outlet arranged in opposing manner across the measuring channel, the barrier gas inlet is in connection with the gas source and provided with a nozzle having a nozzle opening being directed towards the opposing barrier gas outlet having a barrier gas outlet opening,
wherein the barrier arrangement is arranged to provide pressurized gas creating a barrier gas curtain between the barrier gas inlet and the barrier gas outlet hereby providing an area of low pressure so as to force at least a part of the gaseous medium from the supply channel into the measuring channel and entrained by the barrier gas curtain and discharged with the barrier gas curtain through the barrier gas outlet and so as to separate the gaseous medium from the first and second optical units, such that the optical measurement path passes through the barrier gas curtain, and
wherein the barrier arrangement comprises a curtain controller for controlling a flow rate of the barrier gas curtain,
wherein the method comprises steps of:
- providing a pressure difference between a first pressure of the gaseous medium near the inlet supply opening and a second pressure of the gaseous medium near the outlet supply opening, so as to force the gaseous medium from the supply inlet opening toward the supply outlet opening;
- providing a flow of the barrier gas through the nozzle opening toward the barrier gas outlet opening, so as to provide a barrier gas curtain and so as to force at least a part of the gaseous medium from the supply channel into the measuring channel towards the barrier gas curtain;
- controlling the flow rate of the barrier gas curtain, and thereby controlling an amount of the gaseous medium forced towards the barrier gas curtain; and
- measuring the gaseous medium in the measuring channel using the optical arrangement.

16. The method according to claim 15, wherein the gas analyser system further comprises a pressure sensor for measuring and controlling pressure within the gas analyser system, and wherein the method further comprises a step of measuring the pressure difference between the first pressure of the gaseous medium near the inlet supply opening and the second pressure of the gaseous medium near the outlet supply opening and providing a data output accordingly using the pressure system.

17. The method according to claim 16, further comprising a step of controlling the pressure difference between the first pressure of the gaseous medium near the inlet supply opening and the second pressure of the gaseous medium near the outlet supply opening based on the data output using the pressure system.

18. The method according to claim 15, wherein the pressure system comprises a first pressure sensor arranged to measure the first pressure of the gaseous medium near the inlet supply opening and a second pressure sensor arranged to measure the second pressure of the gaseous medium near the outlet supply opening, and provides a first data output and a second data output accordingly and wherein the method further comprises a step of calculating the pressure difference between the first pressure of the gaseous medium near the inlet supply opening and the second pressure of the gaseous medium near the outlet supply opening by subtracting the measured second pressure from the measured first pressure.

19. The method according to claim 16, wherein the pressure system comprises a pressure controller arranged to control the second pressure of the gaseous medium near the outlet supply opening, and wherein the method further comprises a step of controlling the pressure difference based on the data output by controlling the second pressure of the gaseous medium near the outlet supply opening using the pressure controller.

20. The method according to claim 15, further comprising a step of providing the barrier gas curtain from the barrier gas inlet to the barrier gas outlet, wherein the barrier gas curtain is of a width larger or equal to a width of the measuring channel.

* * * * *